United States Patent [19]

Yokoyama et al.

[11] 4,132,851
[45] Jan. 2, 1979

[54] PROCESS FOR PRODUCING QUINAZOLONE DERIVATIVES

[75] Inventors: Yasukazu Yokoyama, Tokyo; Eiji Iwamoto, Yamato, both of Japan

[73] Assignee: Toyo Soda Manufacturing Co., Ltd., Yamaguchi, Japan

[21] Appl. No.: 774,048

[22] Filed: Mar. 3, 1977

[30] Foreign Application Priority Data

Mar. 16, 1976 [JP] Japan .................................. 51/27718

[51] Int. Cl.$^2$ ........................................... C07D 471/22
[52] U.S. Cl. ................................. 544/245; 96/1.5 R; 96/1.6
[58] Field of Search ................... 260/256.4 F, 279 QA

[56] References Cited

U.S. PATENT DOCUMENTS

| | | | |
|---|---|---|---|
| 3,024,239 | 3/1962 | Caliezi | 260/279 QA |
| 3,475,436 | 10/1969 | Cooper et al. | 260/279 QA |
| 3,738,988 | 6/1973 | Jackson | 260/279 QA |
| 3,888,665 | 6/1975 | Wiedermann | 96/1.5 R |
| 4,025,518 | 5/1977 | Wriede | 260/279 QA |

FOREIGN PATENT DOCUMENTS

| | | | |
|---|---|---|---|
| 51-42724 | 4/1976 | Japan. | |
| 894610 | 4/1962 | United Kingdom | 260/256.4 F |
| 909602 | 10/1962 | United Kingdom | 260/256.4 F |

OTHER PUBLICATIONS

Labana et al., "Chemical Reviews", vol. 67, 1967, p. 4.
Gibian, et al., "Chemical Abstracts", vol. 70, 1969.
"Chemical Abstracts", vol. 72, 1970.
Yokoyama et al., "Chemical Abstracts", vol. 83, 1975.

*Primary Examiner*—Nicholas S. Rizzo
*Assistant Examiner*—James H. Turnipseed
*Attorney, Agent, or Firm*—Oblon, Fisher, Spivak, McClelland & Maier

[57] ABSTRACT

6,7,14,15-Tetrahydropyrido[2,1-b]pyrido[1',2':1,2-]pyrimido[4,5-g]quinazoline-7,15-dione is oxidized with a quinone as an oxidizing agent to produce 7,15-dihydropyrido[2,1-b]pyrido[1',2':1,2]pyrimido[4,5-g]quinazoline-7,15-dione.

11 Claims, No Drawings

PROCESS FOR PRODUCING QUINAZOLONE DERIVATIVES

BACKGROUND OF THE INVENTION

1. Field of the Invention

The present invention relates to a process for producing quinazolone derivatives which are useful as pigments and electrophotographic pigments.

2. Description of the Prior Art 7,15-Dihydropyrido[2,1-b]pyrido[1',2':1,2-]pyrimido[4,5-g]quinazoline-7,15-dione and derivatives thereof are useful as organic red pigment and electrophotographic pigment.

It has been known to produce the compounds by heating 6,7,14,15-tetrahydropyrido[2,1-b]pyrido[1',2':1,2]pyrimido[4,5-g]quinazoline-7,15-dione and derivatives thereof in nitrobenzene, glacial acetic acid and piperidine (U.S. Pat. No. 3,888,665).

The inventors have previously invented an improved process for producing the former compounds in which the later compounds were reacted in alkaline conditions (Japanese Unexamined Patent Publication No. 42724/1976). In the improved process, the reaction is carried out in an alkaline condition whereby a ring-opened compound is produced. In order to convert the compound to the object product, it is necessary to acidify the reaction mixture after the reaction for the recycliation, whereby the operation is complicated. Also, it has been necessary to use an expensive organic solvent.

SUMMARY OF THE INVENTION

It is an object of the present invention to provide a process for producing a 7,15-dihydropyrido[2,1-b]pyrido[1',2':1,2]pyrimido[4,5-g]quinazoline-7,15-dione having the formula

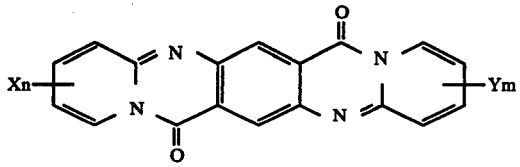

wherein X and Y respectively represent a $C_1 - C_3$ alkyl group, a $C_1 - C_3$ alkoxy group or a halogen atom and n and m respectively represent 0,1 or 2, the compound hereinafter referred to as compound having the formula I, in which a 6,7,14,15-tetrahydropyrido[2,1-b]pyrido[1',2':1,2]pyrimido[4,5-g]quinazoline-7,15-dione having the formula

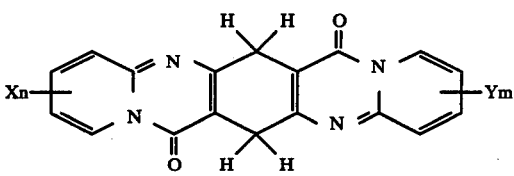

wherein X, Y, n and m are same as defined as above, the later compound hereinafter referred to as compound having the formula II, is oxidized to the compound having formula I.

It is an another object of the present invention to provide a process for producing the compound having the formula I in a smooth reaction without a complicated operation in high yield.

It is a further object of the present invention to provide a process for producing the compound having the formula I suitable for use as pigment.

The object of the present invention has been attained by oxidizing the compound having the formula II with a quinone in a liquid medium in an acidic condition.

DETAILED DESCRIPTION OF THE PREFERRED EMBODIMENTS

Suitable liquid medium used in the reaction of the invention include water, alcohols and organic acids such as acetic acid. A mineral acid such as sulfuric acid, hydrochloric acid or an organic acid such as acetic acid is added to provide an acidic condition for the reaction system. When an acid such as sulfuric acid, organic acids, etc. is used as the liquid medium, it is unnecessary to add an acid to provide an acidic condition.

An amount of the liquid medium is not critical and is preferably about 3 to 50 times to the amount of the compound having the formula II.

Suitable quinones as the oxidizing agent include benzoquinone, halobenzoquinones such as tetrachloro-p-benzoquinone, cyanobenzoquinones such as dichlorodicyanobenzoquinone etc.

An amount of the quinone is more than 1 mole preferably 1 to 3 moles especially 1.0 to 1.2 moles per 1 mole of the compound having the formula II.

The oxidation of the invention is carried out by reacting the compound having the formula II with the quinone as the oxidizing agent in the liquid medium at 60° to 150° C. preferably 100° to 130° C.

The reaction time is dependent upon the reaction temperature, the kinds of the medium and the quinone as the oxidizing agent and is preferably in a range of 30 minutes to 4 hours.

When the object compound having the formula I is used as a pigment, it is preferable to produce it by reacting them in conc. sulfuric acid, adding dropwise the reaction mixture into an organic solvent after the reaction and adding a base to neutralize and separating the precipitated fine crystals whereby the pigmentation step can be combined to obtain fine crystals of the compound having the formula I which has excellent tinting strength and is suitable as pigment.

The invention will be further illustrated by cerain specific examples which are included for purposes of illustration only and not intended to be limiting unless otherwise specified. In the example, the term of "part" means "part by weight".

EXAMPLE 1

In a 1 liter flask equipped with a reflux condenser, 10 wt. parts of 6,7,14,15-tetrahydropyrido[2,1-b]pyrido[1',2':1,2]pyrimido[4,5-g]quinazoline-7,15-dione, 10 wt. parts of p-benzoquinone and 500 wt. parts of $2N-H_2SO_4$ were charged, and the reaction was carried out for 1 hour under refluxing condition.

After the reaction, the reaction mixture was cooled and neutralized with an aqueous solution of sodium hydroxide to obtain red precipitate. The red precipitate was separated by a filtration and washed with 2 wt.% aqueous solution of sodium hydroxide, water and then with acetone to remove excess of benzoquinone and hydroquinone. The product was dried to obtain 10 wt. parts of red crystals of 7,15-dihydropyrido[2,1-b]pyrido[1',2':1,2]pyrimido[4,5-g]quinazoline-7,15-dione. (Yield: 100%). Purity = At least 98%

EXAMPLE 2

A mixture of 10 wt. parts of 6,7,14,15-tetrahydropyrido[2,1-b]pyrido[1',2':1,2]pyrimido[4,5-g]quinazoline-7,15-dione and 8 wt. parts of tetrachloro-p-benzoquinone in 100 wt. parts of conc. sulfuric acid was heated at 120° to 130° C. for 3 hours.

After cooling, tetrachloro-p-benzoquinone and tetrachlorohydroquinone which were not dissolved in conc. sulfuric acid, were separated by filtration of the reaction mixture by a glass filter No. 4. The resulting conc. sulfuric acid solution was added dropwise into 300 parts by volume of methanol under cooling with an ice water to form yellow precipitate.

After the addition, the reaction mixture was neutralized with 30% aqueous solution of sodium hydroxide to precipitate red fine crystals. The precipitate was separated by filtration and was washed with hot water and then was dried to obtain 10 wt. parts of red crystals of 7,15-dihydropyrido[2,1-b]pyrido[1',2':1,2]pyrimido[4,5-g]quinazoline-7,15-dione. (Yield: 100%). Purity = At least 98%

The fine crystals could be used as red pigment without further treatment.

EXAMPLE 3

In the reactor of Example 1, 10 wt. parts of 6,7,14,15-tetrahydropyrido[2,1-b]pyrido[1',2':1,2]pyrimido[4,5-g]quinazoline-7,15-dione, 10 wt. tetrachloro-p-benzoquinone and 200 wt. parts of glacial acetic acid were heated for 4 hours under refluxing condition to precipitate reddish organge crystals.

After cooling the reaction mixture, the crystals were separated by filtration and washed with acetone. The resulting reddish orange needle-like crystals (17 wt. parts) were dispersed in 100 wt. parts of conc. sulfuric acid to dissolve the soluble part.

The resulting conc. sulfuric acid was poured into 300 wt. parts of ice water to precipitate yellow crystals. The product was neutralized with an aqueous solution of sodium hydroxide to form red crystals. The crystals were separated by a filtration and washed with water and dried to obtain 9.5 wt. parts of 7,15-dihydropyrido[2,1-b]pyrido[1',2':1,2]pyrimido[4,5-g]quinazoline-7,15-dione. (Yield: 94.5%). Purity = 91%

The red crystals could be used as red pigment.

EXAMPLE 4

A mixture of 10 wt. parts of 6,7,14,15-tetrahydro-2,10-dimethylpyrido[2,1-b]pyrido[1',2':1,2-]pyrimido[4,5-g]quinazoline-7,15-dione and 4 wt. parts of p-benzoquinone in 100 wt. parts of conc. sulfuric acid, was heated at 120° to 130° C. for 3 hours.

After the reaction, the reaction mixture was cooled and poured into 300 wt. parts of ice water to precipitate yellow crystals. The product was neutralized with an aqueous solution of sodium hydroxide to form red crystals.

The crystals were separated by filtration and washed with hot water and with acetone until forming a colorless filtrate and were dried to obtain 9.5 wt. parts of 7,15-dihydro 2,10-dimethylpyrido[2,1-b]pyrido[1',2':1,2]pyrimido[4,5-g]quinazoline-7,15-dione. (Yield: 95%). Purity = 90%

The red crystals could be used as pigment without further treatment.

EXAMPLE 5

In the reactor of Example 1, 15 wt. parts of 6,7,14,15-tetrahydropyrido[2,1-b]pyrido[1',2':1,2]pyrimido[4,5-g]quinazoline-7,15-dione, 12 wt. parts of 2,3-dichloro-5,6-dicyano-p-benzoquinone and 300 wt. parts of glacial acetic acid were heated for 1 hour under refluxing condition to precipitate reddish organge crystals.

After cooling the reaction mixture, the crystals were separated by filtration and washed with water and acetone. The resulting crystals were dispersed in 300 wt. parts of 2 wt.% aqueous solution of sodium hydroxide.

The dispersion was filtered and the resulting red crystals were thoroughly washed with water and dried to obtain 14.5 wt. parts of 7,15-dihydropyrido[2,1-b]pyrido[1',2':1,2]pyrimido[4,5-g]quinazoline-7,15-dione. (Yield: 94.5%, Purity = 93%

EXAMPLE 6

10 Wt. parts of 6,7,14,15-tetrahydro-3,11-dimethylpyrido[2,1-b]pyrido[1',2':1,2]pyrimido[4,5-g]quinazoline-7,15-dione and 4 wt. parts of o-benzoquinone were reacted in the similar way as in Example 1.

The reaction mixture was treated in the same way as in Example 1 to obtain 10 wt. parts of 7,15-dihydro 3,11-dimethylpyrido[2,1-b]pyrido[1',2':1,2-]pyrimido[4,5-g]quinazoline-7,15-dione.

REFERENCE 1

In a 300 ml four necked flask, 20 wt. parts of 6,7,14,15-tetrahydropyrido[2,1-b]pyrido[1',2':1,2-]pyrimido[4,5-g]-quinazoline-7,15-dione, 200 wt. parts of nitrobenzene, 20 wt. parts of glacial acetic acid and 0.5 wt. part of piperidine were charged and the mixture was heated at 140° to 150° C. for 6 hours under refluxing condition.

The reaction mixture was filtered with suction at 50° C. and was washed with ethanol and was dried.

According to the infrared spectrographic analysis, the unreacted 6,7,14,15-tetrahydropyrido[2,1-b]pyrido[1',2':1,2]pyrimido[4,5-g]quinazoline-7,15-dione was remained as main component though the object product of 7,15-dihydropyrido[2,1-b]pyrido[1',2':1,2]pyrimido[4,5-g]quinazoline-7,15-one was contained. The purity of the object compound in the product was 22% and the reminder 78% was of the unreacted starting material.

What is claimed is:

1. A process for producing a 7,15-dihydropyrido[2,1-b]pyrido[1',2':1,2]pyrimido[4,5-g]quinazoline-7,15-dione having the formula

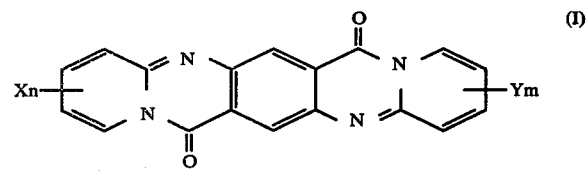

wherein X and Y are each independently selected from the group consisting of $C_1$–$C_3$ alkyl, $C_1$–$C_3$ alkoxyl and halogen, and n and m respectively represent 0, 1 or 2; which comprises the step of oxidizing a 6,7,14,15-tetrahydropyrido[2,1-b]pyrido[1',2':1,2]pyrimido[4,5-g]quinazoline-7,15-dione having the formula

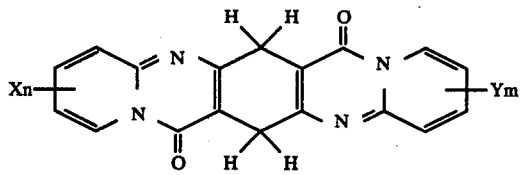

wherein X, Y, n and m are as defined above, with a quinone in an acidic liquid medium selected from the group consisting of concentrated sulfuric acid, glacial acetic acid, aqueous sulfuric acid, aqueous hydrochloric acid and aqueous acetic acid.

2. A process according to claim 1, wherein 6,7,14,15-tetrahydropyrido[2,1-b]pyrido[1',2':1,2]pyrimido[4,5-g]quinazoline-7,15-dione having the formula (II) wherein n and m are 0, is used as the starting material.

3. A process according to claim 1, wherein 6,7,14,15-tetrahydropyrido[2,1-b]pyrido[1',2':1,2]pyrimido[4,5-g]quinazoline-7,15-dione having the formula (II) wherein X and Y are respectively methyl group is used as the starting material.

4. A process according to claim 1, wherein said quinone is benzoquinone or tetrachloro-p-benzoquinone.

5. A process according to claim 1, wherein said liquid medium is acetic acid, sulfuric acid or an aqueous solution thereof.

6. A process according to claim 1, wherein said oxidation is performed at 60° C. to 130° C.

7. A process for producing 7,15-dihydropyrido[2,1-b]pyrido[1',2':1,2]pyrimido[4,5-g]quinazoline-7,15-dione having the formula

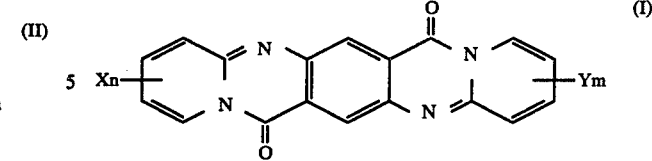

wherein X and Y are each independently selected from the group consisting of $C_1$–$C_3$ alkyl, $C_1$–$C_3$ alkoxyl or halogen, and n and m respectively represent 0, 1 or 2; which comprises the steps of oxidizing a 6,7,14,15-tetrahydropyrido[2,1-b]pyrido[1',2':1,2]pyrimido[4,5-g]quinazoline-7,15-dione having the formula

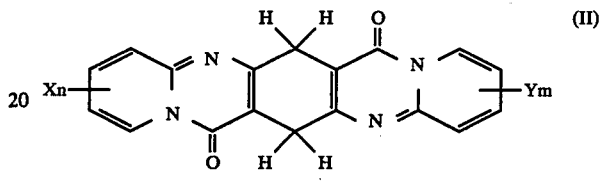

wherein X, Y, n and m are as defined above, with a quinone is concentrated sulfuric acid and pouring the reaction mixture into ice water with or without a filtration and neutralizing the resulting dispersion containing the precipitated crystals and separating the resulting crystals.

8. A process according to claim 7, wherein 6,7,14,15-tetrahydropyrido[2,1-b]pyrido[1',2':1,2]pyrimido[4,5-g]quinazoline-7,15-dione having the formula (II) wherein n and m are 0, is used as the starting material.

9. A process according to claim 7, wherein 6,7,14,15-tetrahydropyrido[2,1-b]pyrido[1',2':1,2]pyrimido[4,5-g]quinazoline-7,15-dione having the formula (II) wherein X and Y are respectively methyl group is used as the starting material.

10. A process according to claim 7, wherein said quinone is benzoquinone or tetrachloro-p-benzoquinone.

11. A process according to claim 7, wherein said oxidation is performed at 60° C. to 130° C.

* * * * *